United States Patent
Reder et al.

(10) Patent No.: US 12,129,238 B2
(45) Date of Patent: Oct. 29, 2024

(54) CRYSTALLINE FORM OF PROPOXAZEPAM, THE METHOD OF ITS MAKING AND USE AS MEDICINAL AGENT

(71) Applicants: Anatoliy Reder, Odessa (UA); Dmytro Pozigun, Odessa (UA)

(72) Inventors: Anatoliy Reder, Odessa (UA); Dmytro Pozigun, Odessa (UA)

( * ) Notice: Subject to any disclaimer, the term of this patent is extended or adjusted under 35 U.S.C. 154(b) by 801 days.

(21) Appl. No.: 17/415,821

(22) PCT Filed: Jan. 30, 2019

(86) PCT No.: PCT/UA2019/000020
§ 371 (c)(1),
(2) Date: Jun. 18, 2021

(87) PCT Pub. No.: WO2020/131000
PCT Pub. Date: Jun. 25, 2020

(65) Prior Publication Data
US 2022/0073474 A1 Mar. 10, 2022

(30) Foreign Application Priority Data
Dec. 20, 2018 (UA) .............................. a 2018 12659

(51) Int. Cl.
*C07D 243/24* (2006.01)
*A61P 25/02* (2006.01)

(52) U.S. Cl.
CPC ............ *C07D 243/24* (2013.01); *A61P 25/02* (2018.01); *C07B 2200/13* (2013.01)

(58) Field of Classification Search
CPC ........ A61P 25/02; A61P 29/00; C07D 243/24; C07B 2200/13; A61K 31/5513
See application file for complete search history.

(56) References Cited

U.S. PATENT DOCUMENTS

| | | | |
|---|---|---|---|
| 4,432,987 A | 2/1984 | Barth et al. | |
| 5,721,359 A | 2/1998 | Dunn et al. | |
| 7,145,002 B2 | 12/2006 | Brands et al. | |

FOREIGN PATENT DOCUMENTS

| | | |
|---|---|---|
| GB | 1022642 | 3/1966 |
| UA | 108246 C2 | 4/2015 |

(Continued)

OTHER PUBLICATIONS

Pavlovsky V.I. et al. Analgesic Effects of 3-Substituted Derivatives of 1,4-Benzodiazepines and their Possible Mechanisms, Neurophysiology, vol. 45, Nos. 5/6, 2013, pp. 427-432, Fig. 1-3, compound 6.

(Continued)

*Primary Examiner* — Sarah Pihonak
*Assistant Examiner* — Padmaja S Rao
(74) *Attorney, Agent, or Firm* — Lathrop GPM LLP; Brian C. Tringue

(57) ABSTRACT

The invention relates to a crystalline form of the Compound (I), wherein the crystalline form displays its strongest reflection, stated as a 2Θ value, at 25±0.2°, in an X-ray powder diffraction pattern. The invention also relates to a method of making this crystalline form, as well as pharmaceutical compositions comprising thereof. Furthermore, the invention relates to methods of using this crystalline form as a medicament and in the treatment of pain.

(I)

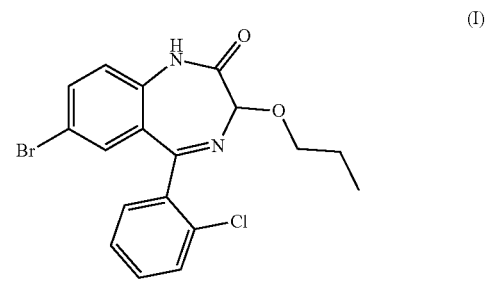

17 Claims, 4 Drawing Sheets

(56) References Cited

FOREIGN PATENT DOCUMENTS

WO     WO 2003/051275 A2     6/2003
WO          2018067102 A1     4/2018

OTHER PUBLICATIONS

International Search Report for International Application No. PCT/UA2019/000020, dated Aug. 13, 2019.

Brittain HG, "Polymorphism in Pharmaceutical Solids", Drugs and Pharmaceutical Sciences, vol. 95, Marcel & Dekker Inc. (15$^{th}$ Edition), Chapter 5.

Guidance for Industry, ANDAs: Pharmaceutical Solid Polymorphism, Chemistry, Manufacturing and Controls Information, Jul. 2007.

International Examination Report for Application No. AP/P/2021/013352 issued by African Regional Intellectual Property Organization mailed Sep. 25, 2023, 3 pages.

CRYSTALLINE FORM OF PROPOXAZEPAM, THE METHOD OF ITS MAKING AND USE AS MEDICINAL AGENT

RELATED APPLICATIONS

This application is a 35 U.S.C. § 371 filing of International Application No. PCT/UA2019/000020, filed Jan. 30, 2019, which claims priority to Ukraine Patent Application No. a 2018 12659, filed Dec. 20, 2018, the contents of each of which are incorporated herein by reference in their entirety. P The invention relates to a crystalline form of compound (I), (I)

wherein the crystalline form displays its strongest reflection, stated as a 2Θ value, at 25±0.2°, in an X-ray powder diffraction pattern. The invention also relates to a method of making the crystalline form, as well as pharmaceutical compositions comprising the crystalline form. Furthermore, the invention relates to methods of using this crystalline form as a medicament and in the treatment of pain:

BACKGROUND TO THE INVENTION

Compound (I) (7-Bromo-3-propoxy-5-(2-chlorophenyl)-1,3-dihydrobenzo-[e]-[1,4]-diazepin-2-one) is a compound known in the art. For instance, 7-bromo-3-propoxy-5-(2-chlorophenyl)-1,3-dihydrobenzo-[e]-[1,4]-diazepin-2-ones and a method for its synthesis are described in Ukrainian patent No. 108246 ("Use of 3-alkoxy-1,2-dihydro-3H-1,4-benzdiazepin-2-ones as highly active analgesic agents", Pavlovskii V, Semenishina K, Andronaty S, Kabanova T, Khalimova O, Reder A; application No. a 2013 01685; Patent published 10 Apr. 2015, Bulletin No. 7).

WO 2018/067102 relates to medical chemistry, in particular to the use of 7-bromo-5-(o-chlorophenyl)-3-propoxy-1,2-dihydro-3H-1,4-benzodiazepin-2-one as a drug which inhibits neuropathic pain without the formation of defects in the gastric mucosa (ulcerogenic effect), and possesses an anticonvulsant property.

The crystal state of a compound can be important when the compound is used for pharmaceutical purposes. Compared with an amorphous solid, the solid physical properties of a crystalline compound can change, which can affect its suitability for pharmaceutical use.

Polymorphism is the ability of a solid material to exist in more than one crystalline form, each of which has different orientations and/or conformations of molecules in the crystal lattice. Each crystal state, or "polymorph", exhibits a unique set of physicochemical properties due to differences in crystal structure.

In addition, polymorphic forms may have different mechanical properties, such as fluidity and compactability, which affect the technological properties of the compound. Stability and duration of storage of the compound may also depend on the polymorph.

Polymorphs can be distinguished from each other in different ways. Polymorphs clearly exhibit spectroscopic properties, and they can be determined using, for example, infrared spectroscopy, Raman spectroscopy, and 13C-NMR spectroscopy. In view of the fact that each crystalline form refracts X-rays in different ways, X-ray powder diffraction (XPD) can also be used to characterize polymorphs. In addition, thermal methods such as differential scanning calorimetry (DSC) and thermogravimetric analysis (TTA) can provide unique information on a particular polymorph.

Figure 1:
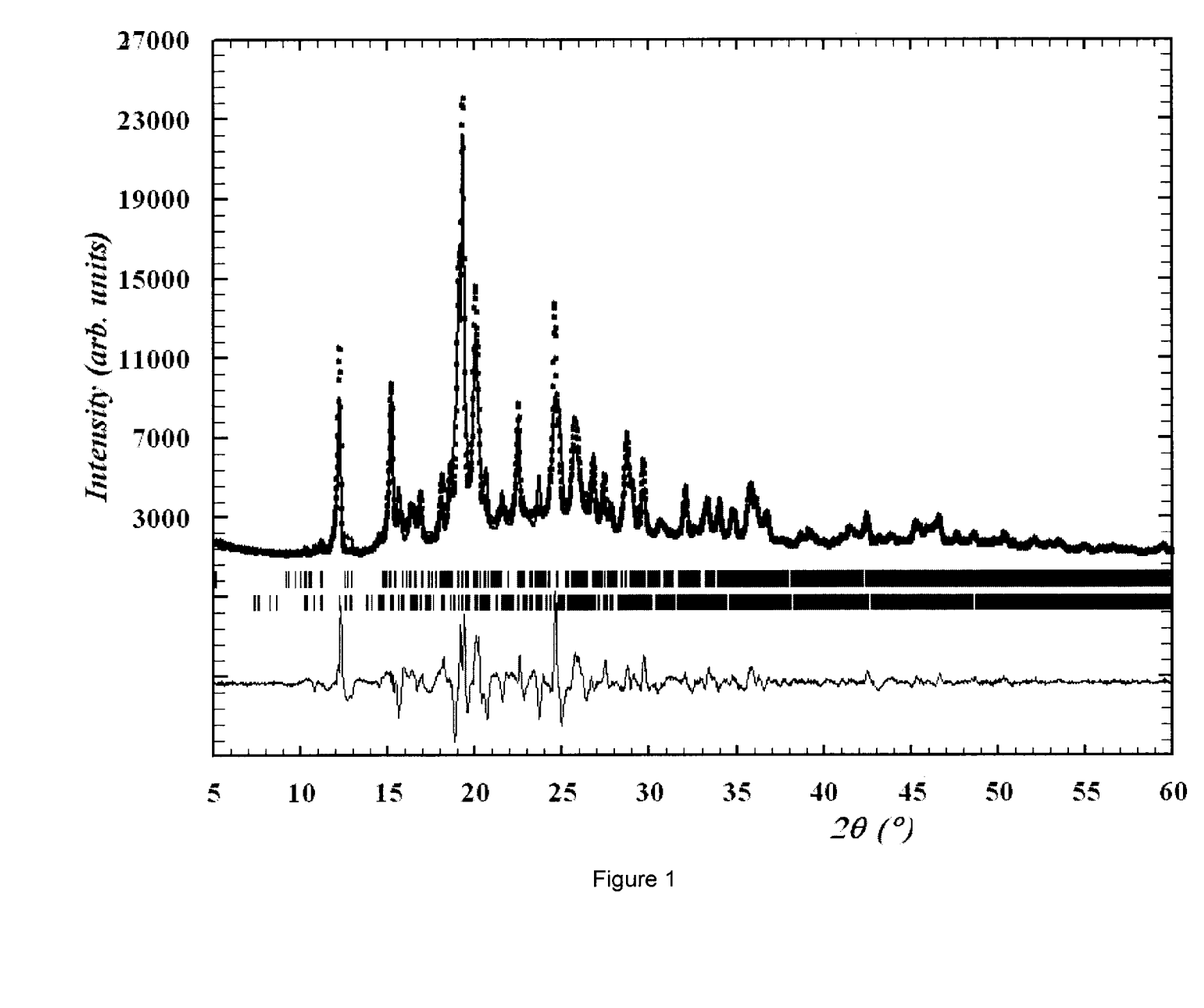
FIG. 1 shows the X-ray powder diffraction pattern of the crystalline compound described in Ukrainian patent No. 108246 and WO 2018/067102 (Form I/Comparative Example 1).
Figure 2:
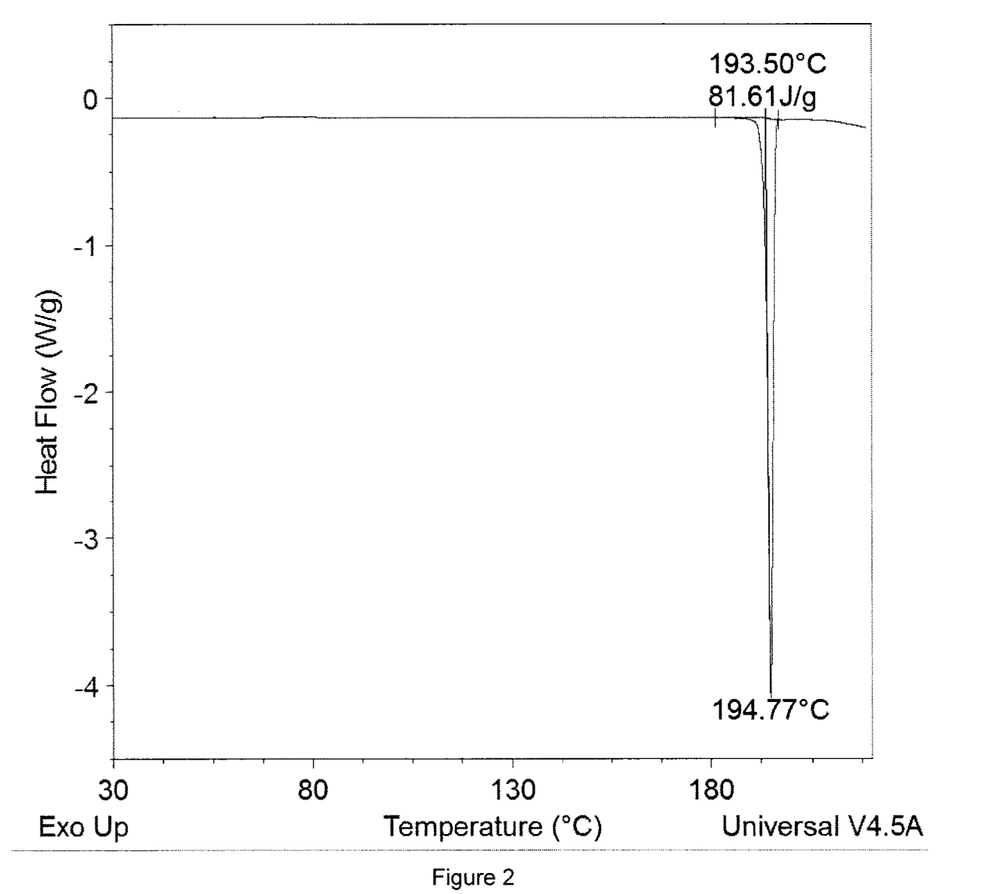
FIG. 2 shows the DSC thermogram of the crystalline compound described in Ukrainian patent No. 108246 and WO 2018/067102 (Form I/Comparative Example 1).

It has been found that compound (I) described in Ukrainian patent No. 108246 and WO 2018/067102 has a particular crystalline structure, herein denoted "Form I". FIG. 1 shows the X-ray powder diffraction pattern of the crystalline compound described in Ukrainian patent No. 108246 and WO 2018/067102. As shown in FIG. 1, the strongest reflection, stated as a 2Θ value, is at about 19°. FIG. 2 shows a DSC thermogram of a sample of the crystalline compound described in Ukrainian patent No. 108246 and WO 2018/067102. As shown in FIG. 2, an endothermic transition is observed with approximate temperature of 195° C. Form I therefore has a melting point of about 195° C.

The following objects were based in the invention:

It is one object of the present invention to overcome at least some of any disadvantages of the prior art or to provide a commercially useful alternative thereto.

It is a further object of the present invention to provide a crystalline form having an enhanced or similar analgesic effect compared to known crystalline forms of compound (I).

It is a further object of the present invention to provide a crystalline form which exhibits an enhanced or similar bioavailability compared to known crystalline forms of compound (I) or compositions thereof.

It is a further object of the present invention to provide a crystalline form which exhibits a reduced or similar toxicity compared to known crystalline forms of compound (I) or compositions thereof.

The task is solved

In a first aspect the present invention provides a crystalline form of compound (I), (I)

wherein the crystalline form displays its strongest reflection, stated as a 2Θ value, at 25±0.2°, in an X-ray powder diffraction pattern.

Each aspect or embodiment as defined herein may be combined with any other aspect(s) or embodiment(s) unless clearly indicated to the contrary. In particular any feature indicated as being preferred or advantageous may be combined with any other feature or features indicated as being preferred or advantageous.

In a further aspect the present invention provides a method of making the crystalline form as described herein, the method comprising:
(i) dissolving compound (I) in dimethylsulfoxide to provide a solution of compound (I) in dimethylsulfoxide;
(ii) adding the solution of compound (I) in dimethylsulfoxide to water to provide a suspension of compound (I);
(iii) allowing the suspended compound (I) in the suspension of compound (I) to precipitate to provide the crystalline form as described herein.

In a further aspect the present invention provides a pharmaceutical composition comprising the crystalline form as described herein, and at least one pharmaceutically acceptable excipient.

In a further aspect the present invention provides the crystalline form as described herein, or the pharmaceutical composition as described herein, for use in therapy.

In a further aspect the present invention provides the crystalline form as described herein, or the pharmaceutical composition as described herein, for use as a medicament.

In a further aspect the present invention provides the crystalline form as described herein, or the pharmaceutical composition as described herein, for use in treating or preventing neuropathic pain.

In a further aspect the present invention provides the crystalline form as described herein, or the pharmaceutical composition as described herein, for use in treating or preventing nociceptive pain.

In a further aspect the present invention provides the crystalline form as described herein, or the pharmaceutical composition as described herein, for use in treating or preventing diabetic neuropathy.

In a further aspect the present invention provides a method of treating or preventing neuropathic pain in a human or animal patient comprising administering to a patient in need thereof an effective amount of a crystalline form as described herein, or the pharmaceutical composition as described herein.

In a further aspect the present invention provides a method of treating or preventing nociceptive pain in a human or animal patient comprising administering to a patient in need thereof an effective amount of a crystalline form as described herein, or the pharmaceutical composition as described herein.

In a further aspect the present invention provides a method of treating or preventing diabetic neuropathy in a human or animal patient comprising administering to a patient in need thereof an effective amount of a crystalline form as described herein, or the pharmaceutical composition as described herein.

Other preferred embodiments of the compounds according to the invention appear throughout the specification and in particular in the examples.

The present inventors have surprisingly found that the crystalline form of the present invention has an enhanced or similar analgesic effect compared to known crystalline forms of compound (I).

The present inventors have surprisingly found that the crystalline form of the present invention exhibits an enhanced or similar bioavailability compared to known crystalline forms of compound (I) or compositions thereof.

The present inventors have surprisingly found that the crystalline form of the present invention exhibits a similar toxicity compared to known crystalline forms of compound (I) or compositions thereof.

Without wishing to be bound by theory, it is thought that the crystalline form of the present invention tends to show the advantageous effects discussed above due to its crystal structure.

DETAILED DESCRIPTION OF THE INVENTION

Unless otherwise defined herein, scientific and technical terms used in connection with the present invention shall have the meanings that are commonly understood by those of ordinary skill in the art. The meaning and scope of the terms should be clear, however, in the event of any latent ambiguity, definitions provided herein take precedent over any dictionary or extrinsic definition.

The present invention provides a crystalline form of compound (I), (I)

wherein the crystalline form displays its strongest reflection, stated as a 2Θ value, at 25±0.2°, in an X-ray powder diffraction pattern.

Unless explicitly stated to the contrary, all X-ray powder diffraction patterns are determined using copper radiation.

Preferably the crystalline form further displays one or more reflections, stated as a 2Θ value, at one or more of 17.8±0.2°, 19.4±0.2°, 20.9±0.2° and 27.5±0.2°, in an X-ray powder diffraction pattern. More preferably the crystalline form further displays two or more reflections, stated as 2Θ values, at two or more of 17.8±0.2°, 19.4±0.2°, 20.9±0.2° and 27.5±0.2°, in an X-ray powder diffraction pattern. More preferably still the crystalline form further displays three or more reflections, stated as 2Θ values, at three or more of 17.8±0.2°, 19.4±0.2°, 20.9±0.2° and 27.5±0.2°, in an X-ray powder diffraction pattern. Most preferably the crystalline form further displays four reflections, stated as 2Θ values, at all of 17.8±0.2°, 19.4±0.2°, 20.9±0.2° and 27.5±0.2°, in an X-ray powder diffraction pattern.

Preferably the X-ray powder diffraction pattern of the crystalline form described herein does not display a reflection, stated as a 2Θ value, at 15.1±0.2°.

Preferably the crystalline form has a melting point of 186° C. to 191° C. More preferably the crystalline form has a melting point of 187° C. to 190° C. More preferably still the crystalline form has a melting point of 187.5° C. to 189.5° C. Most preferably the crystalline form has a melting point of about 188° C. to about 189° C.

Unless explicitly stated to the contrary, melting points are determined using differential scanning calorimetry (DSC).

The present invention provides a method of making the crystalline form as described herein, the method comprising:
(i) dissolving compound (I) in dimethylsulfoxide to provide a solution of compound (I) in dimethylsulfoxide;

(ii) adding the solution of compound (I) in dimethylsulfoxide to water to provide a suspension of compound (I);

(iii) allowing the suspended compound (I) in the suspension of compound (I) to precipitate to provide the crystalline form described herein.

The compound (I) in step (i) may be in any form. For example, the compound (I) in step (I) may be amorphous, or in a crystalline form, such as Form I, which is the crystalline form of compound (I) when prepared according to the process described in Ukrainian patent No. 108246 and WO2018/067102. Preferably the compound (I) in step (i) is in the crystalline form of compound (I) when prepared according to the process described in Ukrainian patent No. 108246 and WO2018/067102.

Preferably the solution of compound (I) in dimethylsulfoxide is a saturated solution of compound (I) in dimethylsulfoxide.

Preferably the step of dissolving compound (I) in dimethylsulfoxide comprises dissolving from 0.5 g to 1.5 g of Compound (I) per 5 to 15 ml of dimethyl sulfoxide. More preferably the step of dissolving compound (I) in dimethylsulfoxide comprises dissolving from 0.75 g to 1.25 g of Compound (I) per 8 to 12 ml of dimethyl sulfoxide. More preferably the step of dissolving compound (I) in dimethylsulfoxide comprises dissolving from 0.9 g to 1.1 g of Compound (I) per 9 to 11 ml of dimethyl sulfoxide.

Preferably, adding the solution of compound (I) in dimethylsulfoxide to water (step (ii)) is carried out at a temperature of from 15° C. to 25° C. More preferably, adding the solution of compound (I) in dimethylsulfoxide to water (step (ii)) is carried out at a temperature of from 17° C. to 23° C., or from 18° C. to 22° C., most preferably from 19° C. to 21° C.

Preferably, adding the solution of compound (I) in dimethylsulfoxide to water (step (ii)) is carried out at a pressure of from 100 KPa to 103 KPa. More preferably, adding the solution of compound (I) in dimethylsulfoxide to water (step (ii)) is carried out at a pressure of from 100.5 KPa to 102.5 KPa, more preferably still from 101 KPa to 102 KPa. Most preferably, adding the solution of compound (I) in dimethylsulfoxide to water (step (ii)) is carried out at about 101.325 KPa (atmospheric pressure).

Preferably the step of adding the solution of compound (I) in dimethylsulfoxide to water (step (ii)) comprises adding from 5 ml to 15 ml of the solution per 50 ml to 150 ml of water. More preferably the step of adding the solution of compound (I) in dimethylsulfoxide to water (step (ii)) comprises adding from 7.5 ml to 12.5 ml of the solution per 75 ml to 125 ml of water. Most preferably the step of adding the solution of compound (I) in dimethylsulfoxide to water (step (ii)) comprises adding from 9 ml to 11 ml of the solution per 90 ml to 110 ml of water.

Preferably, allowing the suspended compound (I) in the suspension of compound (I) to precipitate (step (iii)) is carried out at a temperature of from 15° C. to 25° C. More preferably, allowing the suspended compound (I) in the suspension of compound (I) to precipitate (step (iii)) is carried out at a temperature of from 17° C. to 23° C., or from 18° C. to 22° C., most preferably from 19° C. to 21° C.

Preferably, allowing the suspended compound (I) in the suspension of compound (I) to precipitate (step (iii)) is carried out at a pressure of from 100 KPa to 103 KPa. More preferably, allowing the suspended compound (I) in the suspension of compound (I) to precipitate (step (iii)) is carried out at a pressure of from 100.5 KPa to 102.5 KPa, more preferably still from 101 KPa to 102 KPa. Most preferably, allowing the suspended compound (I) in the suspension of compound (I) to precipitate (step (iii)) is carried out at about 101.325 KPa (atmospheric pressure).

Preferably the suspension provided in step (ii) is mixed/stirred for at least 10 minutes, more preferably at least 15 minutes, more preferably at least 20 minutes, most preferably for about 30 minutes, before the suspended compound (I) is allowed to precipitate in step (iii).

Preferably, the suspended compound (I) in the suspension of compound (I) is allowed to precipitate (step (iii)) over a time period of from 30 minutes to 10 hours, preferably from 1 hour to 7 hours, more preferably from 1 hour to 5 hours, most preferably from 2 hours to 4 hours.

Preferably the process further comprises filtering the crystalline form of compound (I) after it has precipitated in step (iii). Preferably the process further comprises vacuum filtering the crystalline form of compound (I) after it has precipitated in step (iii).

Preferably the process further comprises washing with water, the crystalline form of compound (I) provided in step (iii). Alternatively, preferably, the crystalline form of compound (I) provided in step (iii) is filtered and subsequently washed with water.

Preferably the process further comprises drying the crystalline form of compound (I) provided in step (iii). Alternatively, preferably, the crystalline form of compound (I) provided in step (iii) is filtered and subsequently dried. Alternatively, more preferably, the crystalline form of compound (I) provided in step (iii) is filtered, subsequently washed with water and then dried. Preferably the crystalline form of compound (I) is dried at a temperature of 100° C. to 140° C., more preferably 110° C. to 130° C., most preferably 115° C. to 125° C.

The present invention provides a pharmaceutical composition comprising the crystalline form as described herein, and at least one pharmaceutically acceptable excipient.

Suitable pharmaceutically acceptable excipients would be known by the person skilled in the art, for example, fats, water, physiological saline, alcohol (e.g., ethanol), glycerol, polyols, aqueous glucose solution, extending agent, disintegrating agent, binder, lubricant, wetting agent, stabilizer, emulsifier, dispersant, preservative, sweetener, colorant, seasoning agent or aromatizer, concentrating agent, diluent, buffer substance, solvent or solubilizing agent, chemical for achieving storage effect, salt for modifying osmotic pressure, coating agent or antioxidant, saccharides such as lactose or glucose; starch of corn, wheat or rice; fatty acids such as stearic acid; inorganic salts such as magnesium metasilicate aluminate or anhydrous calcium phosphate; synthetic polymers such as polyvinylpyrrolidone or polyalkylene glycol; alcohols such as stearyl alcohol or benzyl alcohol; synthetic cellulose derivatives such as methylcellulose, carboxymethylcellulose, ethylcellulose or hydroxypropylmethylcellulose; and other conventionally used additives such as gelatin, talc, plant oil and gum arabic.

Preferably the pharmaceutical composition comprises one or more further pharmaceutically active agents.

The present invention provides the crystalline form as described herein, or the pharmaceutical composition as described herein, for use in therapy.

The present invention provides the crystalline form as described herein, or the pharmaceutical composition as described herein, for use as a medicament.

The present invention provides the crystalline form as described herein, or the pharmaceutical composition as described herein, for use in treating or preventing neuropathic pain. Preferably, the neuropathic pain is central neuropathic pain. Alternatively, preferably, the neuropathic pain is peripheral neuropathic pain.

The present invention provides the crystalline form as described herein, or the pharmaceutical composition as described herein, for use in treating or preventing nociceptive pain.

The present invention provides the crystalline form as described herein, or the pharmaceutical composition as described herein, for use in treating or preventing neuropathic pain.

There is also provided the use of the crystalline form as described herein, or the pharmaceutical composition as described herein, for the manufacture of a medicament for treating or preventing neuropathic pain. Preferably, the neuropathic pain is central neuropathic pain. Alternatively, preferably, the neuropathic pain is peripheral neuropathic pain.

There is also provided the use of the crystalline form as described herein, or the pharmaceutical composition as described herein, for the manufacture of a medicament for treating or preventing diabetic neuropathy.

There is also provided the use of the crystalline form as described herein, or the pharmaceutical composition as described herein, for the manufacture of a medicament for treating or preventing nociceptive pain.

The present invention provides a method of treating or preventing neuropathic pain in a human or animal patient comprising administering to a patient in need thereof an effective amount of a crystalline form as described herein, or the pharmaceutical composition as described herein. Preferably, the neuropathic pain is central neuropathic pain. Alternatively, preferably, the neuropathic pain is peripheral neuropathic pain.

The present invention provides a method of treating or preventing nociceptive pain in a human or animal patient comprising administering to a patient in need thereof an effective amount of a crystalline form as described herein, or the pharmaceutical composition as described herein.

The present invention provides a method of treating or preventing diabetic neuropathy in a human or animal patient comprising administering to a patient in need thereof an effective amount of a crystalline form as described herein, or the pharmaceutical composition as described herein.

When introducing elements of the present disclosure or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

The foregoing detailed description has been provided by way of explanation and illustration, and is not intended to limit the scope of the appended claims. Many variations in the presently preferred embodiments illustrated herein will be apparent to one of ordinary skill in the art, and remain within the scope of the appended claims and their equivalents.

These and other aspects of the invention will now be described with reference to the accompanying Figures, in which.

EXPERIMENTAL SECTION

X-ray powder diffraction studies were carried out using a «Siemens D500» diffractometer (copper radiation, graphite monochromator on the secondary beam, the Bragg-Brentano geometry).

Monocrystalline X-ray studies were carried out on a diffractometer «Xcalibur3» (Molybdenum radiation, graphite monochromator, CCD «Sapphire3» detector, ω-scanning, $2\theta_{MaKC}=50°$) at room temperature (about 20° C.) and at atmospheric pressure (about 101.325 KPa).

Thermographic study was performed on a differential scanning calorimeter DSC Q2000 "Thermo Scientific", heating rate 5° C./min heating range 20-210° C.

Information on the size of the crystals was obtained on a diffractometer Mastersizer 3000 "Malvent"; the substance was introduced into a dispersant containing 1% aqueous sodium lauryl sulfate solution, kept under ultrasound for 5 minutes, laser quenching 8-13%.

Micronization was carried out on a laboratory of Tube Mill control from IKA, Germany, using methods known in the art.

EXAMPLES

The following non-limiting examples further illustrate the present invention.

Comparative Example 1

Compound (I) was prepared as described in Ukrainian patent No. 108246 and WO2018/067102.

A sample of this compound (I) was analysed using powder X-ray diffraction using Copper radiation on a «Siemens D500» diffractometer (copper radiation, graphite monochromator on the secondary beam, the Bragg-Brentano geometry). The X-ray powder diffraction pattern of this compound (I) is shown in FIG. 1. In particular, the strongest reflection, stated as a 2Θ value, is at about 19°. The compound (I) prepared as described in Ukrainian patent No. 108246 and WO2018/067102 has a particular crystalline structure, herein denoted "Form I".

A sample of the same compound (Form I) was analysed using differential scanning calorimetry (DSC). The DSC thermogram is shown in FIG. 2. As shown in FIG. 2, an endothermic transition is observed with approximate temperature of 195° C. Form I therefore has a melting point of about 195° C.

Monocrystalline X-ray studies were also carried out on Form I of Compound I. The results are shown in Table 1 below. Crystals of Form I were obtained by the long isothermic (20° C.) evaporation (approximately 1 month) of a sample of Compound (I) in Form I (Comparative Example 1) previously dissolved in ethyl alcohol in a sample bottle sealed with a lubricant-free glass ground stopper.

Inventive Example 1

Figure 3:
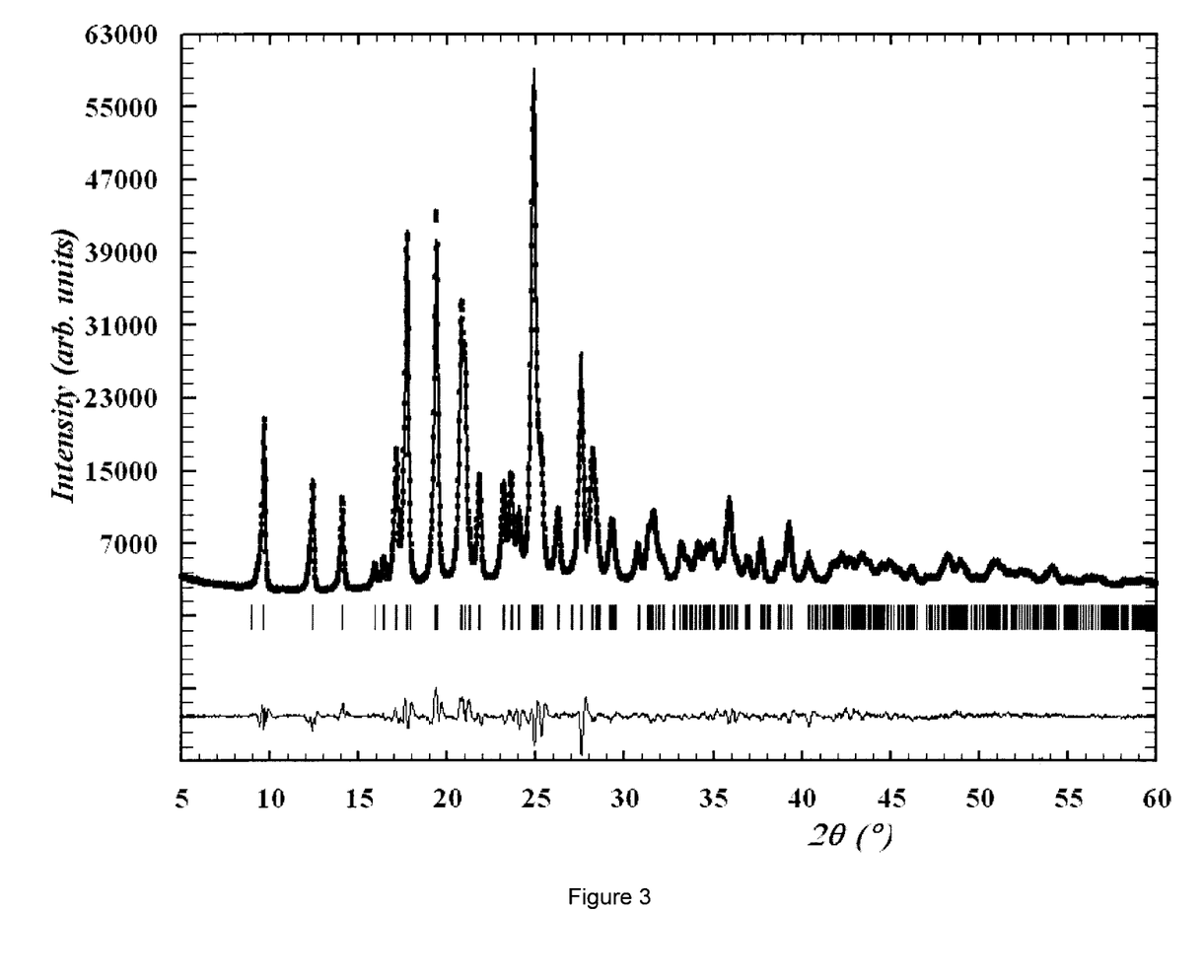
FIG. 3 shows the X-ray powder diffraction pattern of the crystalline form of Inventive Example 1 (Form II).

A sample of Compound (I), prepared as described in Ukrainian patent No. 108246 and WO2018/067102, is dissolved in dimethyl sulfoxide. In particular, 1 g of the sample of Compound (I) is dissolved per 10 ml of dimethyl sulfoxide at room temperature (about 20° C.). The solution obtained is slowly added to water at room temperature (10 ml of the solution per 100 ml of water) under vigorous stirring and the suspension formed is mixed for 30 minutes. The stirring is then stopped and the suspension is left for precipitation for three hours. The dispersed precipitate is vacuum-filtered using filtering paper, washed three times with purified water (100 ml each time) and dried in a drying and heating chamber (universal drying and heating chamber FD-115, available from Binder Gmbh, Germany) at 120° C. The resulting crystalline sample was analysed using powder X-ray diffraction using Copper radiation on a «Siemens D500» diffractometer (copper radiation, graphite monochromator on the secondary beam, the Bragg-Brentano geometry). The X-ray powder diffraction pattern of the resulting sample is shown in FIG. 3. In particular, the strongest reflection, stated as a 2Θ value, is at about 25±0.2°. The crystalline form is denoted as Form II.

Figure 4:
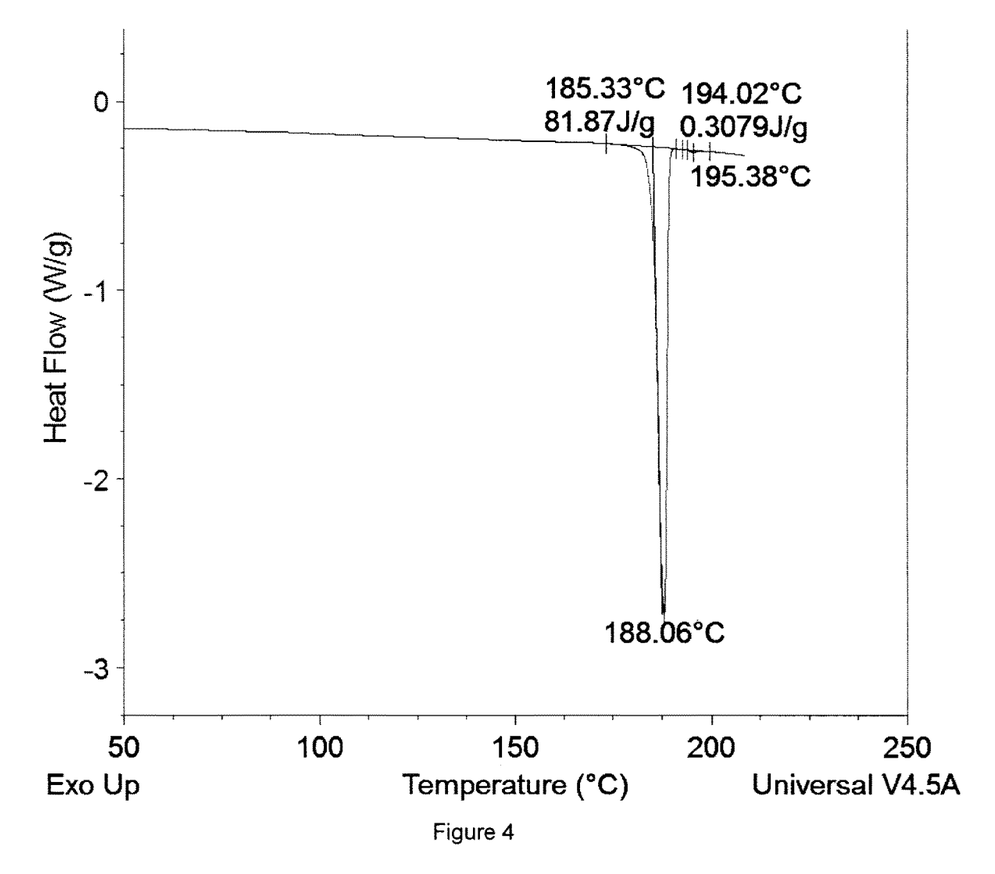
FIG. 4 shows the DSC thermogram of the crystalline form of Inventive Example 1 (Form II).

A sample of Form II was analysed using differential scanning calorimetry (DSC). The DSC thermogram is shown in FIG. 4. As shown in FIG. 4, an endothermic transition is observed with approximate temperature of 188° C. Form II therefore has a melting point of about 188° C.

Monocrystalline X-ray studies were also carried out on Form II of Compound I. To prepare the sample for monocrystalline X-ray study, Form II crystals were obtained by the long isothermic (20° C.) evaporation (approximately one month) of a sample of Compound (I) in Form II (Inventive Example 1) previously dissolved in isobutyl alcohol in a sample bottle sealed with a lubricant-free glass ground stopper. As shown below in Table 1, Form II crystallizes in the monoclinic space group Cc with the parameters of the crystal lattice a=10.9301 (9) A, b=19.7560 (14) A, c=8.5894 (8) A, β=108.165 (11) and a cell volume of 1762.3 (3) A3.

A comparison of the main crystallographic data of two polymorphic forms of Compound I is given in Table 1.

Comparison of Inventive Example 1 and Comparative Example 1

The basic crystallographic data and refinement of structures for the Form I and Form II of Compound I (Monocrystalline data).

TABLE 1

| Sample | Form I | Form II |
| --- | --- | --- |
| The empirical formula | $C_{18}H_{16}BrClN_2O_2$ | |
| $M_r$, a.m.u. | 407.69 | |
| Temperature, T, K | 293 (2) | |
| Wavelenght, λ (MoKα), Å | 0.71073 | |
| Syngony, spatial group | Monoclinic, $P\,2_1/c$ | Monoclinic, Cc |
| The lattice parameters (Å, °) | a = 11.7032 (15), | a = 10.9301 (9); |
|  | b = 21.5185 (17), | b = 19.7560 (14), |
|  | c = 14.509 (2) | c = 8.5894 (8), |
|  | β = 92.867 (12) | β = 108.165 (11) |
| Cell volume V, Å³ | 3649.3 (7) | 1762.3 (3) |
| Quantity of formula units, Z | 8 | 4 |
| Density $d_x$, g/cm³ | 1.484 | 1.537 |
| Attenuation ratio μ (MoKα), Mm⁻¹ | 2.411 | 2.497 |
| Structural factor, $F_{000}$ | 1648 | 824 |
| Crystal size, mm | 0.40 × 0.12 × 0.01 | 0.15 × 0.12 × 0.05 |
| The angle interval, ° | 2.97 ≤ Θ ≤ 26.00 | 3.66 ≤ Θ ≤ 26.00 |
| Index constraint | −13 ≤ h ≤ 14, −26 ≤ k ≤ 26, −17 ≤ l ≤ 17 | −13 ≤ h ≤ 13, −24 ≤ k ≤ 24, −10 ≤ l ≤ 9 |
| Reflections measured/independent | 26808/6741 ($R_{int}$ = 0.202) | 6317/2698 ($R_{int}$ = 0.0971) |
| Coverage, % | 93.9 | 97.4 |
| Transmittion $T_{max}/T_{min}$ | 0.598/0.128 | 0.885/0.706 |
| Refinement method | Full matrix LSM $F^2_{hkl}$ | |
| Data/parameters in LSM | 6741/434 | 2698/222 |
| Goodness of fit, S | 0.980 | 0.964 |
| Flack parameter | — | 0.02 (2) |
| R-factor for the observed refl (I > 2σI) | $R_1$ = 0.0796, wR2 = 0.1357 | $R_1$ = 0.0590, wR2 = 0.1096 |
| The R-factor for refl | $R_1$ = 0.2195, $wR^2$ = 0.1837 | $R_1$ = 0.1137, $wR^2$ = 0.1391 |
| $\Delta\rho_{max}/\Delta\rho_{min}$, E./Å³ | 0.806/−0.364 | 0.381/−0.386 |

Example 2

Determination of the Mean Lethal Dose ($LD_{50}$) of Polymorphic Forms of Compound (I)

The preliminary assignment of a substance to a certain toxicity class is based on an indicator that quantitatively characterizes the acute toxicity of the compound—the dose of the substance that causes a lethal effect in 50% of the population ($LD_{50}$). Determination of this indicator in one of the types of experimental animals allows to extrapolate it for other species and justify the dose limits for the first phase of clinical trials.

To estimate the mean lethal dose of various polymorphic forms of Compound (I) they were administered (in the form of a stabilized suspension on an isotonic sodium chloride solution) at increasing doses orally (one route of administration expected in clinical use, for example) to experimental animals (mice) and the lethal effect was observed in the supervised experimental groups throughout 14 days after administration. To calculate the average dose, mortality/survival rates of the animals by the end of the observation period were used.

The $LD_{50}$ values for samples of Form I and Form II were found to be 1121±190 mg/kg for Form I and 1475±402 mg/kg for Form II. The two $LD_{50}$ values are not statistically significantly different, on the basis of which it can be concluded that in the used doses, the two polymorphic modifications of compound (I) (propoxazepam) have comparable toxicity. Based on the $LD_{50}$ values for orally administered different polymorphic forms, the compound can be assigned to the IV toxicity class (low toxicity compounds), regardless of the polymorphic modification.

Example 3

Analgesic Activity of Crystalline Forms of Compound (I) in the Model of Thermal Nociception ("Tail Flick" Test)

Antinociceptive (analgesic) activity was evaluated on a rat tail "tail-flick" model using a focused light beam on rats. Latency time was determined by tail pulling away from the beam source, expressed in seconds. Animals were randomized with respect to the initial value of the latent period, with index from 4 to 12 seconds. The magnitude of the antinociceptive effect was indicated by the increasing of the length of the latent period (pain sensitivity threshold, PST). The initial indices of the PST and its changes 2 hours after the administration of the test compound were compared. The calculation of $ED_{50}$ (the average effective dose of analgesic activity in this model for rats) was carried out using the least squares method.

Three samples of compound (I) were prepared and used in the 'tail-flick' test:
 The first sample is prepared using the sample of Comparative Example 1, i.e. Form I, in its natural coarse crystalline state. In particular, the coarse crystalline sample of Comparative Example 1 is dispersed in a saline solution and stabilized with Tween 80). The crystalline structure (Form I) remains unchanged.
 The second sample was prepared by micronizing (mechanically grinding) the coarse crystalline sample of Comparative Example 1, in order to prepare a sample of Form I having a smaller average particle size. In particular, the micronized sample is dispersed in a saline solution and stabilized with Tween 80). The crystalline structure (Form I) remains unchanged.

The third sample is a dispersed sample of Inventive Example 1, i.e. compound (I) in crystalline Form II. In particular, a sample of Inventive Example 1 is dispersed in a saline solution and stabilized with Tween 80). The crystalline structure (Form II) remains unchanged. The third sample has a similar average particle size to the second sample for a side-by-side comparison.

The results are shown in Table 2.

TABLE 2

| Crystalline form of Compound (I) | Form I (coarse crystalline) | Form I (micronized) | Form II |
|---|---|---|---|
| Average particle size | (90% of particles by volume <530 microns) | (90% of particles by volume <~50 microns) | (90% of particles by volume <~50 microns) |
| $ED_{50}$ (Average effective dose (50%)), mg/kg | 1.82 | 1.06 | 0.17 |

As shown in Table 2, the value of the average effective dose for Form II (0.17 mg/kg) is substantially lower than for coarse crystalline Form I (1.82 mg/kg). The value of the average effective dose for Form II is also substantially lower (0.17 mg/kg) than for micronized Form I (1.06 mg·kg), despite the average particle sizes being substantially the same (90% of particles by volume<~50 microns).

These results therefore indicate that, with regard to nociceptive pain, Form II (Inventive Example 1) surprisingly displays a higher bioavailability compared to Form I (Comparative Example 1).

Example 4

Analgesic Activity of Crystalline Forms of Compound (I) in the Model of Acetic Acid-Induced Pain (Cramps) on Mice To reproduce acute visceral and somatic deep pain (nociceptive pain), the method of "acetic acid-induced pain (cramps)" was used in mice. The mice received a 0.75% solution of acetic acid intraperitoneally (at a dose of 0.1 ml/10 g of body weight), 2 hours after the administration of the test compounds. The number of cramps was counted from the first to the 20$^{th}$ minute (inclusive) after modeling the pathological state. The calculation of $ED_{50}$ (the average effective dose of analgesic activity in this model for mice) was carried out using the least squares method.

Two samples of compound (I) were prepared and used in the 'tail-flick' test:
 The first sample is a dispersed sample of Form I. This was prepared by adding a hot (65° C.) saturated solution of Comparative Example 1 (Form I) in ethyl alcohol to water at room temperature (about 20° C.) and atmospheric pressure (about 101.325 KPa). Dispersed Form I has a particle size (D(50)) of around 29 μm.
 The second sample is a dispersed sample of Inventive Example 1, i.e. compound (I) in crystalline Form II. This sample is prepared by was dispersing Inventive Example 1 in a saline solution stabilized with Tween-80. The crystalline structure remains unchanged. Dispersed Form II has a particle size (D(50)) of around 24.3 μm.

The results are shown in Table 3.

TABLE 3

| Crystalline form of Compound (I) | Dispersed Form I | Dispersed Form II |
|---|---|---|
| ED$_{50}$ (Average effective dose (50%)), mg/kg | 1.87 mg/kg. | 0.89 mg/kg |

As shown in Table 3, the value of the average effective dose for dispersed Form II (0.89 mg/kg) is substantially lower than for dispersed Form I (1.87 mg/kg). With regard to this pain model (i.e. treatment of nociceptive pain), Form II therefore surprisingly possesses more than double the activity of Form 1. These results therefore indicate that, with regard to nociceptive pain, Form II (Inventive Example 1) surprisingly displays a higher bioavailability compared to Form I (Comparative Example 1).

Compound (I) is known to exhibit analgesic properties, as shown above and in WO2018/067102, for example. The results in Examples 3 and 4 indicate that Form II of compound (I) will display a similar improved bioavailability with regard to neuropathic (central and peripheral) and diabetic neuropathy.

The following essential features allow us to obtain such a technical result—develop an easy way of obtaining a crystalline form of the Compound (I) and a pharmaceutical composition for use in the treatment and prevention of neuropathic pain, the prevention of nociceptive pain.

The invention claimed is:

1. A crystalline form of compound (I), (I)

wherein the crystalline form displays its strongest reflection, stated as a 2θ value, at 25±0.2°, in an X-ray powder diffraction pattern.

2. The crystalline form of claim 1, further displaying one or more reflections, stated as a 2θ value, at one or more of 17.8±0.2°, 19.4±0.2°, 20.9±0.2° and 27.5±0.2°, in an X-ray powder diffraction pattern.

3. The crystalline form of claim 1, wherein the X-ray powder diffraction pattern does not display a reflection, stated as a 2θ value, at 15.1±0.2°.

4. The crystalline form of claim 1, having a melting point of 186° C. to 191° C.

5. The crystalline form of claim 1, having a melting point of 187° C. to 190° C.

6. A method of making the crystalline form of claim 1, the method comprising:
(i) dissolving compound (I) in dimethylsulfoxide to provide a solution of compound (I) in dimethylsulfoxide;
(ii) adding the solution of compound (I) in dimethylsulfoxide to water to provide a suspension of compound (I);
(iii) allowing the suspended compound (I) in the suspension of compound (I) to precipitate to provide the crystalline form as defined in claim 1.

7. The method of claim 6, wherein the solution of compound (I) in dimethylsulfoxide is a saturated solution of compound (I) in dimethylsulfoxide.

8. The method of claim 6, wherein adding the solution of compound (I) in dimethylsulfoxide to water is carried out at a temperature of from 15° C. to 25° C.

9. The method of claim 6, wherein allowing the suspended compound (I) in the suspension of compound (I) to precipitate is carried out at a temperature of from 15° C. to 25° C.

10. A pharmaceutical composition comprising the crystalline form of claim 1, and at least one pharmaceutically acceptable excipient.

11. The pharmaceutical composition of claim 10 comprising one or more further pharmaceutically active agents.

12. A method of treating or preventing neuropathic pain in a human or animal patient comprising administering to a patient in need thereof an effective amount of a crystalline form of claim 1.

13. A method of treating or preventing nociceptive pain in a human or animal patient comprising administering to a patient in need thereof an effective amount of a crystalline form of claim 1.

14. A method of treating or preventing diabetic neuropathy in a human or animal patient comprising administering to a patient in need thereof an effective amount of a crystalline form of claim 1.

15. A method of treating or preventing neuropathic pain in a human or animal patient comprising administering to a patient in need thereof an effective amount of the pharmaceutical composition according to claim 10.

16. A method of treating or preventing nociceptive pain in a human or animal patient comprising administering to a patient in need thereof an effective amount of the pharmaceutical composition according to claim 10.

17. A method of treating or preventing diabetic neuropathy in a human or animal patient comprising administering to a patient in need thereof an effective amount of the pharmaceutical composition according to claim 10.

* * * * *